US012678629B2

(12) United States Patent
   Doerr

(10) Patent No.: US 12,678,629 B2
(45) Date of Patent: Jul. 14, 2026

(54) 5G IMPLANT

(71) Applicant: BIOTRONIK SE & Co. KG, Berlin (DE)

(72) Inventor: Thomas Doerr, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 300 days.

(21) Appl. No.: 18/263,725

(22) PCT Filed: Feb. 2, 2022

(86) PCT No.: PCT/EP2022/052385
   § 371 (c)(1),
   (2) Date: Aug. 1, 2023

(87) PCT Pub. No.: WO2022/171495
   PCT Pub. Date: Aug. 18, 2022

(65) Prior Publication Data
   US 2024/0307698 A1      Sep. 19, 2024

(30) Foreign Application Priority Data
   Feb. 9, 2021      (DE) ......................... 202021100624.2

(51) Int. Cl.
   *A61N 1/37*       (2006.01)
   *A61N 1/372*      (2006.01)
   (Continued)

(52) U.S. Cl.
   CPC ....... *A61N 1/37223* (2013.01); *A61N 1/3956* (2013.01); *G16Y 10/60* (2020.01)

(58) Field of Classification Search
   CPC .......... A61B 2560/0266; A61B 5/0022; A61B 5/0031; A61B 5/4836; A61N 1/37211;
   (Continued)

(56) References Cited

U.S. PATENT DOCUMENTS 10,500,401 B2      12/2019      Hayes
2008/0082144 A1      4/2008      Marcotte et al.
(Continued)

OTHER PUBLICATIONS

International Search Report (PCT/ISA/210) and Written Opinion (PCT/ISA/237) mailed on May 27, 2022, by the European Patent Office as the International Searching Authority for International Application No. PCT/EP2022/052385. (8 pages).

*Primary Examiner* — Amanda K Hulbert
(74) *Attorney, Agent, or Firm* — Buchanan Ingersoll & Rooney PC

(57)      ABSTRACT

The invention relates to a medical device and a method for operating a medical device, said medical device comprising a unit configured to perform at least one function selected from the group of: evaluation of signals, therapy delivery, an interface to a network, in particular a 5G network, the interface being configured to communicate directly or indirectly with the network, wherein the medical device is further configured to directly or indirectly influence the at least one function via the network communication, and a basic supply unit configured to ensure a basic function of the medical device if the network communication is interrupted during intended use of the medical device.

18 Claims, 2 Drawing Sheets

110        120        130        140        150

(51) Int. Cl.
*A61N 1/39* (2006.01)
*G16Y 10/60* (2020.01)

(58) Field of Classification Search
CPC .... A61N 1/37223; A61N 1/39; A61N 1/3956;
G16Y 10/60
See application file for complete search history.

(56) References Cited

U.S. PATENT DOCUMENTS

| | | | |
|---|---|---|---|
| 2011/0230734 A1* | 9/2011 | Fain | A61N 1/37211 600/302 |
| 2014/0029411 A1* | 1/2014 | Nayak | G16H 40/67 370/219 |
| 2017/0181645 A1* | 6/2017 | Mahalingam | A61B 5/74 |
| 2019/0021597 A1 | 1/2019 | Nagy et al. | |
| 2021/0038103 A1* | 2/2021 | Larsen | A61B 5/287 |

* cited by examiner 110    120    130    140    150

110    120    130    140    150

5G IMPLANT

CROSS-REFERENCE TO RELATED APPLICATIONS

This application is the United States National Phase under 35 U.S.C. § 371 of PCT International Patent Application No. PCT/EP2022/052385, filed on Feb. 2, 2022, which claims the benefit of German Patent Application No. 20 2021 100 624.2, filed on Feb. 9, 2021, the disclosures of which are hereby incorporated by reference herein in their entireties.

TECHNICAL FIELD

The present invention relates to a medical device, in particular an active electronic implant.

BACKGROUND

U.S. Publication No. 2019/0021597 A1 discloses a physiologic monitoring system comprising a central hub in communication with a management portal for communicating physiologic measurements taken from a plurality of peripheral devices on a patient. At least one non-invasive peripheral device may measure physiologic data from a patient and be in communication with said central hub. A system including an invasive peripheral device may be associated with said patient and be in communication with said central hub. The central hub may be scalable to collect and communicate measurements from the non-invasive peripheral device and the invasive peripheral device. The at least one non-invasive peripheral device may include a blood pressure cuff, an oxygen sensor, a weight scale, and an ECG monitor. The invasive peripheral device may include a wireless sensor reader that may be adapted to measure physiologic data from a sensor implant placed within the cardiovascular system of said patient.

With regard to the integration of active implants and implant systems or comparable medical devices into 5G-based networks and subsequent network generations, whereby at least one of the implant or device functions is indirectly or directly influenced, controlled and/or evaluated via the 5G network in real time or near real time, there is regularly the challenge of a restricted device function due to temporary interruption of the network connection, which can lead to an unacceptable patient risk. The 5G network is to be understood as a network according to the fifth generation (5G) mobile communications standard. If other networks with a comparable or higher performance are available, these can also be used for the present invention.

The present disclosure is directed toward overcoming one or more of the above-mentioned problems, though not necessarily limited to embodiments that do.

SUMMARY

Based on this, an object of the present invention is to create a medical device which, in the event of an interruption in the network connection, allows the device to function safely and appropriately for clinical use.

At least this object is solved by a medical device having the features of claim 1. Advantageous embodiments of the present invention are described below.

According to claim 1, a medical device is disclosed comprising at least one function for evaluation of signals and/or for therapy delivery, at least one of said functions requiring timely regulation or control or evaluation for correct function, said medical device further comprising an interface to a network (in particular 5G network or comparable or higher level network), said interface being configured to directly or indirectly communicate with said network (e.g., 5G network) on demand, and via the network communication, e.g., 5G network communication, at least one of the functions can be directly or indirectly influenced, and wherein the medical device comprises a basic supply unit corresponding to the at least one function, which is configured to perform minimal functional requirements of the medical device in case the network connection, e.g., the 5G network connection, is interrupted during the intended use of the medical device.

Furthermore, according to claim 13, a computer-implemented method for operating a medical device is provided.

The method comprises performing at least one function selected from the group of evaluation of signals and therapy delivery.

Furthermore, the method comprises communicating directly or indirectly with the network by means of an interface to a network, in particular a 5G network, wherein the medical device is further directly or indirectly influences the at least one function via the network communication.

The method in addition comprises providing a basic function of the medical device by means of a basic supply unit if the network communication is interrupted during intended use of the medical device.

Moreover, the present invention provides a computer program comprising program code for performing the method when the computer program is executed on a computer and a computer-readable data carrier with program code of a computer program for performing the method when the computer program is executed on a computer.

The present invention thus solves an object of ensuring that medical devices, in particular active electronic medical devices, in particular active implants, which comprise real-time influence by a network connection, are in a sufficiently safe operating mode even in the event of a temporary unavailability of the network.

According to an embodiment of the present invention, it is provided that the network, in particular 5G network, has at least a bandwidth of greater than 100 Mbit/sec.

Furthermore, according to an embodiment of the present invention, it is provided that the network, in particular 5G network, has at least a typical latency of less than 10 ms.

Furthermore, according to an embodiment of the present invention, it is provided that the medical device is an active electronic implant for permanent implantation.

Further, according to an embodiment of the present invention, it is provided that the medical device is an active electronic implant for temporary implantation.

Further, according to an embodiment of the present invention, it is provided that the medical device is a battery-powered electronic device for temporary or permanent attachment to the body.

Further, the medical device may be one of the following devices:

- a pacemaker;
- a wireless pacemaker;
- an implantable defibrillator, transvenous or non-transvenous;
- a neurostimulator, any type;
- a cardiac rhythm monitor;
- an implantable sensor for physiological parameters;
- an implantable communication system, e.g., as a relay station for communication with one or more other implants;

an implant for monitoring medical prostheses;

an implant for monitoring patient activity or compliance; and an implant for monitoring the patient's medication intake.

Furthermore, according to an embodiment of the present invention, said interface of the medical device is formed by a first communication interface used for communication between the medical device and a further communication device, and by the further communication device connected to the network, in particular 5G network, via a second communication interface.

Furthermore, according to an embodiment of the present invention, it is provided that the interface of the medical device is directly connected or connectable to the network, in particular the 5G network.

Furthermore, according to an embodiment of the present invention, it is provided that the medical device comprises a detection unit for signaling network interruptions, which activates the basic supply unit.

Furthermore, according to an embodiment of the present invention, it is provided that the medical device comprises a connection quality analysis unit that can predict a probable connection interruption and thus activates or pre-initializes the basic supply unit in advance.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

For a more complete understanding of the present invention and advantages thereof, reference is now made to the following description taken in conjunction with the accompanying drawings. The present invention is explained in more detail below using exemplary embodiments, which are specified in the schematic figures of the drawings, in which.

DETAILED DESCRIPTION 5G network technology is characterized by a significantly higher data rate and, above all, significantly lower latency (~1 ms). Likewise, the spatial availability of this network technology is expected to improve significantly compared to the current network coverage. In addition to established applications for remote data transmission, 5G technology will support real-time applications for the first time, such as autonomous driving.

Here, the present invention particularly exploits the fact of a very short latency of this network technology to be able to realize real-time control of medical devices and, in particular, electronic implants with significantly more complex algorithms and principles.

Figure 1:
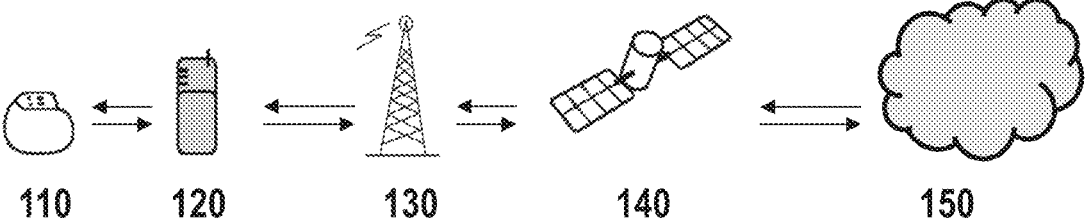
FIG. 1 shows a schematic representation of a medical device controllable via a 5G network according to an embodiment of the present invention.

FIG. 1 shows a 5G network-controlled medical device 110 in the form of an electronic implant, hereinafter also referred to as implant 110. Said implant 110 first transmits to a relay station 120 sensor data recorded by the implant 110. The relay station 120 may be formed as a device (owned) by the patient, for example, a cell phone or smart phone. This first transmission link is required for energy reasons, as the power supply and antenna arrangement, i.e., body attenuation, of this implant 110 are not designed for direct communication with a 5G network. The sensor data is then transmitted to a 5G network via base station 130 and/or a 5G satellite 140 to a cloud-based real-time evaluation system 150, where it is evaluated and control signals derived therefrom are transmitted back to the implant 110 in real time via the aforementioned communication system, so that an implant function, such as therapy delivery or therapy adjustment, can be performed directly here. The difference between this and automated remote programming of an implant is that the influence on the control function occurs in near real time, and thus essential implant algorithms for implant control can be relocated to the cloud-based evaluation system 150.

Figure 2:
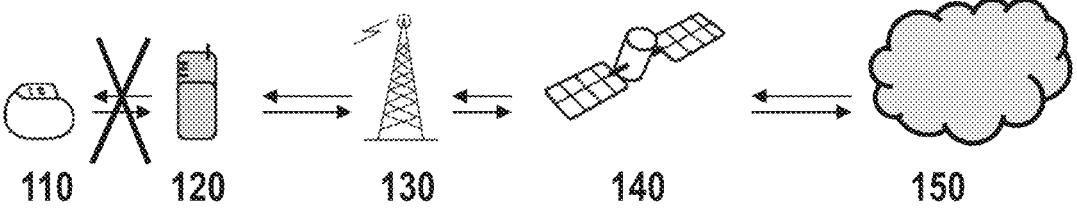
FIG. 2 shows a schematic representation of a basic supply unit for ensuring a basic function of the medical device in case of a network failure according to the embodiment of the present invention.

In FIG. 2, a temporary interruption of the 5G network connection is shown, here for example, between implant 110 and relay station 120. In this situation, real-time influence of the implant function cannot be maintained. In this case, the implant will detect the broken connection and activate a basic supply unit, which is configured in such a way that it secures the basic function of the implant. For example, in the example of an implantable defibrillator, this may be the activation of a simplified detection function for ventricular fibrillation that triggers a defibrillation function when a maximum rate is exceeded, but forgoes the therapy decisions for lower rates (VT/SVT discrimination) supported by the 5G network.

Another specific example of such an application (not shown) is disclosed as a non-transvenous defibrillator. In such a system, the challenge is to have to make a defibrillation therapy decision on a signal very similar to the surface ECG. These signals are influenced by many factors, such as externally coupled disturbances, muscle potentials, changes in patient position, motion artifacts, etc., so that current systems have limited sensitivity and specificity with respect to defibrillation therapy.

If such a defibrillator is implemented according to the present invention, the ECG signals are sent to the cloud-based evaluation system 150 before a therapy decision is made. If there is a need for therapy, these signals are evaluated using considerably more complex algorithms, and within a very short time the implant's therapy decision is confirmed or revoked. Again, in the event of a disruption of the 5G network, a basic function of the defibrillator can be provided with the basic supply unit.

The present invention enables completely new, more complex possibilities for the control and evaluation of medical devices, in particular active implants due to the network connection according to the present invention. By means of the basic supply unit, the basic function of the respective medical device can be ensured with advantage.

Figure 3:
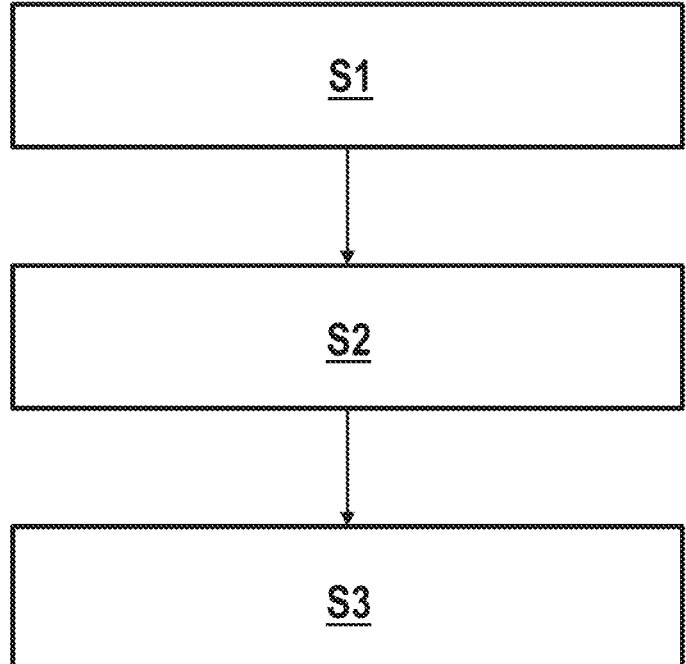
FIG. 3 shows a flowchart of a computer-implemented method for operating a medical device failure according to the embodiment of the present invention.

FIG. 3 shows a flowchart of a computer-implemented method for operating a medical device failure according to the embodiment of the present invention.

The method comprises performing S1 at least one function selected from the group of evaluation of signals and therapy delivery.

Furthermore, the method comprises communicating S2 directly or indirectly with the network by means of an interface to a network, in particular a 5G network, wherein the medical device 110 is further directly or indirectly influences the at least one function via the network communication.

The method in addition comprises providing S3 a basic function of the medical device 110 by means of a basic supply unit if the network communication is interrupted during intended use of the medical device 110.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

REFERENCE SIGNS

110 medical device
120 relay station
130 base station
140 5G satellite
150 cloud-based evaluation system
S1-S3 method steps
The invention claimed is:

1. A medical device comprising:
a unit configured to perform at least one function selected from the group of: evaluation of signals, or therapy delivery,
an interface to a network, the interface being configured to establish a network communication facilitating direct or indirect communication with a node of the network, wherein the medical device is further configured to directly or indirectly influence the at least one function via the network communication, and
a basic supply unit configured to activate a basic function of the medical device when the network communication is interrupted during intended use of the medical device,
wherein:
the medical device comprises a detection unit for signaling network interruptions, which activates the basic supply unit,
the medical device comprises a connection quality analysis unit configured to predict a probable connection interruption and configured to activate or pre-initialize the basic supply unit in advance, and
the medical device is an implantable defibrillator, wherein the network is a 5G network with a bandwidth of greater than 100 Mbit/sec and/or has at least a latency of less than 10 ms, wherein the basic function activated by the basic supply unit is a simplified detection function for ventricular fibrillation that triggers a defibrillation function when a maximum rate is exceeded and/or forgoes treatment decisions for lower rates supported by the 5G network.

2. The medical device of claim 1, wherein the network has at least a bandwidth of greater than 100 Mbit/sec and/or has at least a latency of less than 10 ms.

3. The medical device of claim 1, wherein the medical device is an active electronic implant for permanent or temporary implantation.

4. The medical device of claim 1, wherein the medical device is a battery-powered electronic device for temporary or permanent attachment to the body.

5. The medical device of claim 1, wherein the medical device is one of a cardiac pacemaker, a wireless pacemaker, an implantable defibrillator, a cardiac rhythm monitor, an implantable sensor for physiological parameters, an implantable communication system, an implant for monitoring medical prostheses, an implant for monitoring patient activity or compliance and an implant for monitoring the patient's medication intake.

6. The medical device of claim 1, wherein the interface of the medical device is formed by a first communication interface used for communication between the medical device and a further communication device, and by the further communication device connected to the network via a second communication interface.

7. The medical device of claim 1, wherein the interface of the medical device is directly connected or connectable to the network.

8. A medical device comprising:
a unit configured to perform at least one function selected from the group of: evaluation of signals, or therapy delivery,
an interface to a network, the interface being configured to establish a network communication facilitating direct or indirect communication with a node of the network, wherein the medical device is further configured to directly or indirectly influence the at least one function via the network communication, and
a basic supply unit configured to activate a basic function of the medical device when the network communication is interrupted during intended use of the medical device,
wherein the network communication facilitates direct or indirect communication with plural nodes of the network, the plural nodes including: i) a relay station; and 2) a base station and/or a satellite, wherein the medical device transmits to the relay station sensor data recorded by the implant, wherein the sensor data is transmittable via the network via the base station and/or the satellite to a cloud-based real-time evaluation system where it is analyzed and real-time control signals derived therefrom are transmittable back to the implant via said network communication.

9. The medical device of claim 8, wherein the medical device is a non-transvenous defibrillator, wherein ECG signals are sent to the cloud-based evaluation system before a therapy decision is made, wherein if a need for therapy is determined, said signals are evaluated, and within a predetermined time period the therapy decision is confirmed or revoked.

10. The medical device of claim 8, wherein the network has at least a bandwidth of greater than 100 Mbit/sec and/or has at least a latency of less than 10 ms.

11. The medical device of claim 8, wherein the medical device is an active electronic implant for permanent or temporary implantation.

12. The medical device of claim 8, wherein the medical device is a battery-powered electronic device for temporary or permanent attachment to the body.

13. The medical device of claim 8, wherein the medical device is one of a cardiac pacemaker, a wireless pacemaker, an implantable defibrillator, a cardiac rhythm monitor, an implantable sensor for physiological parameters, an implantable communication system, an implant for monitoring medical prostheses, an implant for monitoring patient activity or compliance and an implant for monitoring the patient's medication intake.

14. The medical device of claim 8, wherein the interface of the medical device is formed by a first communication interface used for communication between the medical device and a further communication device, and by the further communication device connected to the network via a second communication interface.

15. The medical device of claim 8, wherein the interface of the medical device is directly connected or connectable to the network.

16. A computer-implemented method for operating a medical device, comprising the steps of:

performing at least one function selected from the group of: evaluation of signals, or therapy delivery;

communicating directly or indirectly with a node of a network by means of an interface establishing a network communication with the node, wherein the medical device directly or indirectly influences the at least one function via the network communication;

predicting a probable connection interruption and to activate or pre-initialize a basic supply unit in advance;

detecting signaling network interruptions to activate the basic supply unit; and activating a basic function of the medical device by means of the basic supply unit when the network communication is interrupted during intended use of the medical device, wherein the medical device is an implantable defibrillator, wherein the network is a 5G network with a bandwidth of greater than 100 Mbit/sec and/or has at least a latency of less than 10 ms, wherein the basic function activated by the basic supply unit is a simplified detection function for ventricular fibrillation that triggers a defibrillation function when a maximum rate is exceeded and/or forgoes treatment decisions for lower rates supported by the 5G network.

17. The computer program comprising program code for performing the method according to claim 16 when the computer program is executed on a computer.

18. The computer-readable data carrier with program code of a computer program for performing the method according to claim 16 when the computer program is executed on a computer.

* * * * *